United States Patent
Jackson et al.

(10) Patent No.: US 7,034,243 B2
(45) Date of Patent: Apr. 25, 2006

(54) APPARATUS FOR ELECTRICALLY DISINTEGRATING HYPODERMIC NEEDLE

(76) Inventors: Kenneth A. Jackson, 4666 CR 50, Glenmont, OH (US) 44628; Robert Ochsendorf, 794 Morrison Rd., Columbus, OH (US) 43230; Dane Donohue, 131 Timmerman Rd., Mansfield, OH (US) 44903

( * ) Notice: Subject to any disclaimer, the term of this patent is extended or adjusted under 35 U.S.C. 154(b) by 137 days.

(21) Appl. No.: 10/478,824

(22) PCT Filed: May 28, 2002

(86) PCT No.: PCT/US02/16777

§ 371 (c)(1),
(2), (4) Date: Nov. 21, 2003

(87) PCT Pub. No.: WO02/096592

PCT Pub. Date: Dec. 5, 2002

(65) Prior Publication Data

US 2005/0072758 A1    Apr. 7, 2005

Related U.S. Application Data

(60) Provisional application No. 60/294,088, filed on May 29, 2001.

(51) Int. Cl.
*B23K 11/22* (2006.01)
*A61L 11/00* (2006.01)
*A61G 12/00* (2006.01)

(52) U.S. Cl. .................................................... 219/68
(58) Field of Classification Search ................. 219/68
See application file for complete search history.

(56) References Cited

U.S. PATENT DOCUMENTS

| 4,628,169 A | * | 12/1986 | Ch'ing-Lung | ............... 219/68 |
| 5,091,621 A | * | 2/1992 | Butler | ........................ 219/68 |
| 5,147,304 A | * | 9/1992 | Fladung | ..................... 604/110 |

FOREIGN PATENT DOCUMENTS

| FR | 2719991 A1 | * | 11/1995 |
| FR | 2770407 A1 | * | 5/1999 |
| GB | 2297230 A | * | 7/1996 |
| JP | 2000-262617 A | * | 9/2000 |

* cited by examiner

*Primary Examiner*—Geoffrey S. Evans
(74) *Attorney, Agent, or Firm*—Jerry Semer

(57) ABSTRACT

A device used to disable hypodermic needles uses a power supply (10) and two electrodes (12,14) in a housing. One electrode is placed over the other electrode and slants down towards the other. A collar is used to ensure that when the hypodermic needle is inserted in the device, it will hit the electrodes at the proper point. When the hypodermic needle contacts both electrodes, electricity will flow from the power supply through the lower electrode and up the needle to the top electrode. The electrical resistance of the needle is very high so that it quickly heats up to cause disintegration of the needle.

48 Claims, 5 Drawing Sheets

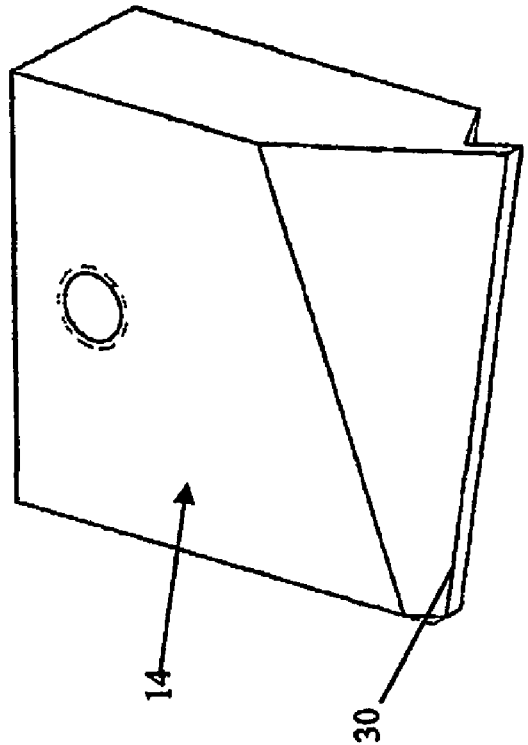
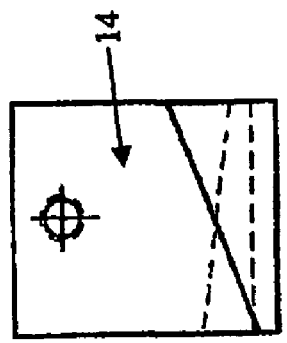
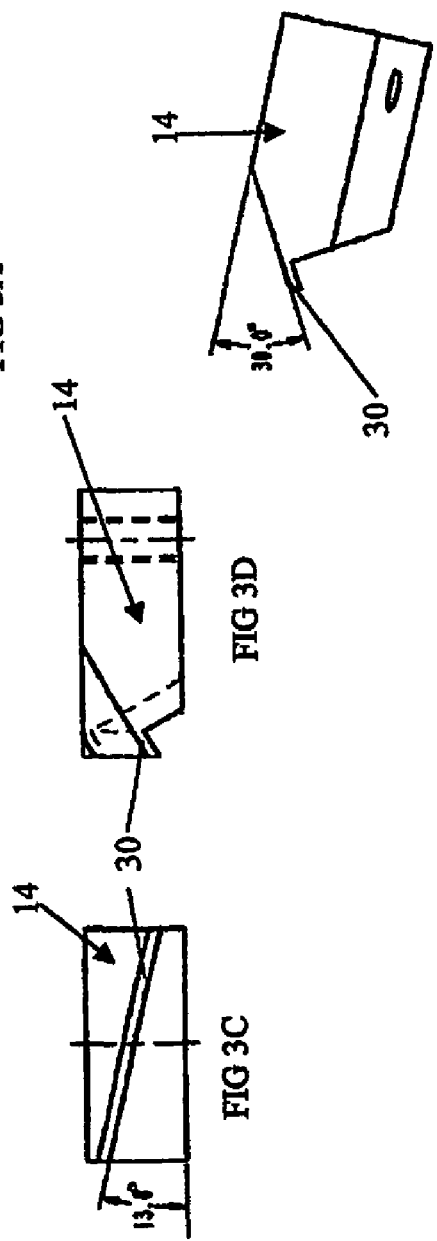
FIG 3A
FIG 3B
FIG 3C
FIG 3D
FIG 3E

APPARATUS FOR ELECTRICALLY DISINTEGRATING HYPODERMIC NEEDLE

This application is a 371 PCT/US02/16777 filed May 28, 2002 which claims benefit of U.S. provisional application 60/294,088 filed May 29, 2001.

FIELD OF THE INVENTION

The present invention relates to the field of needle disabling devices and, more particularly, to the field of needle disabling devices that use current to flow through the needle and heat the needle to a temperature that disintegrates the needle.

BACKGROUND OF THE INVENTION

Each year there are a significant number of people, especially healthcare workers, who are infected with blood-borne diseases through the inadvertent needle pricks from a hypodermic needle. A needle prick can lead to a very serious disease. In this connection, because needle pricks provide direct access to the venous system of the individual, it is possible for such person to contact serious diseases, such as AIDS or hepatitis B through an inadvertent needle prick. The most common time for these needle pricks to occur is when the hypodermic needle is being prepared for disposal or after actual disposal and in the process of destroying said needles. Thus, medical and waste disposal personnel are exposed to a serious risk of injury, infection and disease and even death due to contaminated medical instruments such as hypodermics which are known in the industry as "sharps".

There are many well-documented cases of injury caused by these hypodermic needles or sharps, even while the sharp is encased during transportation to a waste site and during the process of destroying or burying the waste. Hypodermic needles have caused injuries in land fills, and the needles have even been known to wash up on beaches. As long as a needle remains sharp, there is a risk of injury and infection.

The main method of disposal of hypodermic needles today is to deposit the needle in a thick-walled plastic container immediately after use. These containers are then shipped to waste processing sites where they are typically incinerated. However, during this process, the container remains very susceptible to puncture. Also, the contaminated sharps or hypodermic needles may injure and infect individuals attempting to insert the needles into the containers. There are also several health hazards associated with incineration of the hypodermic needles due to the toxic byproducts of the incineration. Also, there is always a problem that these hypodermic needles will escape the medical waste disposal system and expose many people to health risks.

Thus, one of the objectives of this invention is to provide a device that will destroy the "sharps" or the hypodermic needle at the point of use. By destroying the hypodermic needle right at use, greatly reduces the chances of injury for the individual using the needle, and further, it virtually eliminates the possibility of a person being stuck by the needle in the disposal process or afterwards.

Another objective of this invention is to make the device small and light weight so that it can be easily used by health care personal, veterinarians, diabetics, etc. Further, an objective of this invention is to make the device portable and battery operated. The inventor also wished to make the device easy to operate and easy and inexpensive to manufacture. There have been numerous attempts in the prior art to produce a small, light weight, needle-disposing apparatus that could be easily used by healthcare professionals. Patents have been granted on needle-disposing apparatuses to Ch'ing-Lung, U.S. Pat. No. 4,628,169, Spinello, U.S. Pat. No. 4,877,934, Perk, U.S. Pat. No. 5,138,124, Burden, et al, U.S. Pat. No. 5,212,362 and Walker, et al, U.S. Pat. No. 528,964.

All these patents use electricity to destroy the needle. However, they differ from the invention described in this application in that they all use basically an "arc-welding theory" to "dead short" the needle across two electrodes. Thus, the needle is actually placed between two electrodes, then the electricity flows through the width of the needle. There are several problems created by shorting the needle to destroy it. The first thing, the electrodes must make contact at the very bottom of the needle. If the electrodes do not make contact at the very bottom of the needle, the needle will be cut into pieces and a large portion of the needle may not be destroyed. Thus, in all these patents, either the electrodes move or, as in U.S. Pat. Nos. 4,877,934, 5,212, 362, and 5,513,814, the needle must be moved. Thus, one of the objectives of this invention is to create a device for eliminating hypodermic needles that incorporate stationary electrodes. By making the electrodes stationary, one cuts down on the number of parts used and the complexity of the design and, thus, makes the manufacturing of the device easier and cheaper.

Applicant's device does not use the "arc-welding" theory of a dead short across the needle to eliminate the needle. Applicant's device uses "resistance" theory. In the applicant's device, the electric does not flow across the width of the needle, but flows up the length of the needle. When the needle is placed in the device, the electrodes make contact with the bottom and the top of the stainless steel needle. Electric flows from the bottom electrode to the top electrode through the needle, and since the needle is made out of stainless steel, it is very high in resistance. Thus, the needle heats and disintegrates. This process is almost instantaneous. This process also eliminates another problem caused by the dead-short or arc-weld theory. In the dead-short or arc-weld theory, the electric is transferred across the width of the needle and only a small portion of the needle is heated to the temperature to disintegrate at a time. This means that the needle is disintegrated one point of the time. Points above the needle end where it is being disintegrated are not treated to a high temperature. This could cause aerosols to be created by liquids or solids left on the needle. The invention described in this application treats the whole needle immediately to a high temperature and immediately kills any germs or viruses that may be present on the needle.

Another unique feature of this invention which the inventor has not found in the prior art is the collar in which the needle is inserted into the device. This collar has been designed to accept any type of hypodermic needle the inventor knows of on the market. The collar has also been designed to ensure the syringe with the needle will stop at a specific point on the electrode so that it will be fully disintegrated. As I stated above, one of the problems with the prior art is the needle can be inserted too far within the machine and be cut off or cut into a piece and not fully disintegrated.

SUMMARY OF THE INVENTION

The present invention is a device used to disable hypodermic needles of the type currently being used by the medical industry, veterinarians, diabetics, drug abusers, and others. The device has three main parts: a power supply and two electrodes. One electrode is placed over the other and slants down towards the other. The device also has a housing for the electrodes and the power supply, and a collar that ensures that when the hypodermic needle is inserted into the device, it will hit the electrodes at the proper point. To use, one places a hypodermic needle in the collar and slowly rocks the hypodermic in the collar. The hypodermic needle first makes contact with the top electrode, and then as it moves down, it makes contact with the bottom electrode. The electricity from the power supply flows through the bottom electrode, up the hypodermic needle to the top electrode. The resistance of the hypodermic needle is very, very high. Thus, the electric flowing through the hypodermic needle quickly heats the hypodermic needle to a temperature where the needle disintegrates. The collar and the electrodes have been designed to keep the needle syringe positioned so it can be disabled without the possibility that it can be pushed too far into the electrodes. The collar has also been designed to accept all sizes of syringes presently on the market.

BRIEF DESCRIPTION OF THE DRAWINGS

FIG. 3A is a perspective view of the other electrode of the invention.

FIG. 3B is a top view of the other electrode of the invention.

FIG. 3C is a front view of the other electrode of the invention.

FIG. 3D is a side view of the other electrode of the invention.

FIG. 3E is a side perspective view of the other electrode of the invention.

FIG. 4D is a side perspective view of one of the collar of the

DETAILED DESCRIPTION OF THE PREFERRED EMBODIMENT

Figure 1:
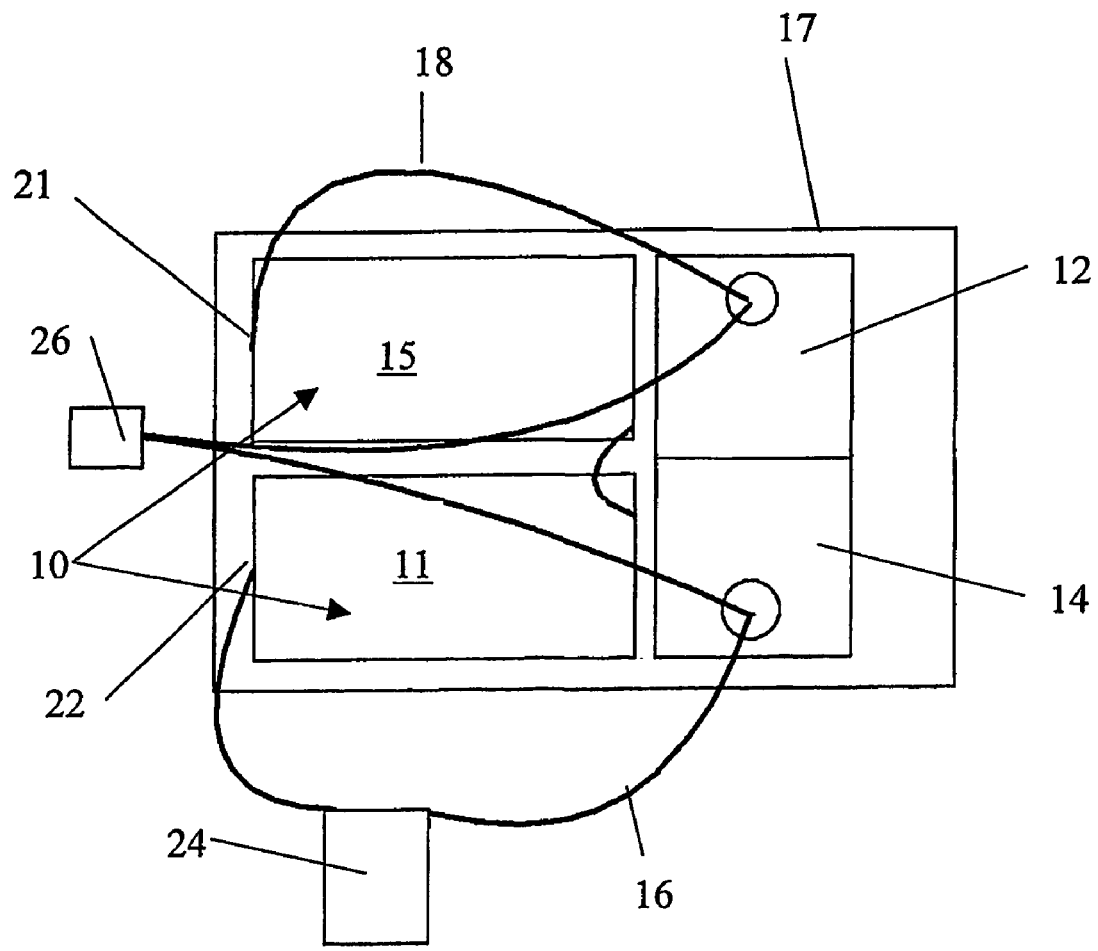
FIG. 1 is a top view of the invention with the top of the housing removed.

FIG. 1 shows the invention with the top of the housing removed. FIG. 1 shows the three main parts of the invention. FIG. 1 shows the power supply 10 which in the preferred embodiment is comprised of two batteries 11 and 15. FIG. 1 also shows the two electrodes 12 and 14. The batteries 11 and 15 are hooked to the two electrodes 12 and 14 by positive wire 16 and negative wire 18. Positive wire 16 hooks to the positive terminal 22 of the battery 11 and runs to electrode 14. Negative wire 18 is hooked to the negative terminal 21 of the battery 15 and runs to electrode 12. Also shown in FIG. 1 is the bottom half of the housing 17 of the invention 20. Hooked into the circuit between the batteries positive terminal 22 and electrode 12 on wire 16 is a fuse 24. The device runs on 12 volts. Also in the preferred embodiment, the device can not only be run from the batteries 11 and 15, but also from a 12 volt power supply. This could be a standard 12 volt wall transformer. FIG. 1 shows a jack 26 which is where a standard wall transformer could be plugged. The jack 26 is hooked to the two electrodes 12 and 14 by positive wire 28 and negative wire 30. The device can be run by any standard wall transformer that produces 12 volt DC around 30 amps.

Figures 2A, 2B, 2C, 2D, 2E:
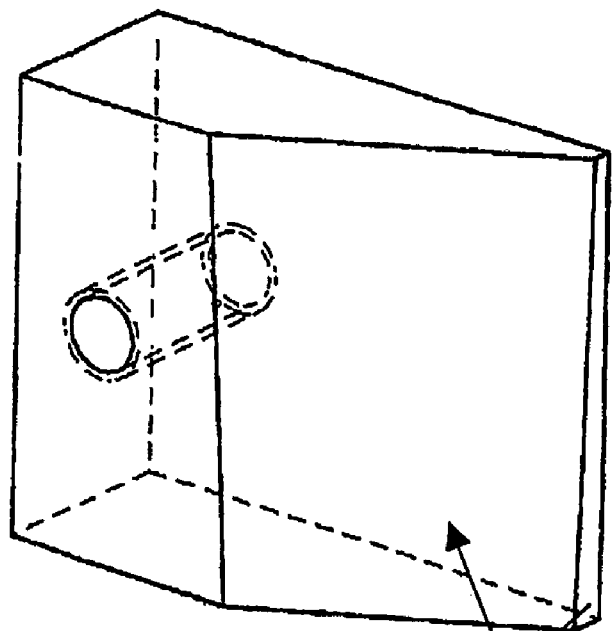
FIG. 2A is a perspective view of one of the electrodes of the invention.
FIG. 2B is a top view of one of the electrodes of the invention.
FIG. 2C is a front view of one of the electrodes of the invention.
FIG. 2D is a side view of one of the electrodes of the invention.
FIG. 2E is a side perspective view of one of the electrodes of the invention.

FIGS. 2A, B, C, D and E show electrode 12. FIG. 2A is a perspective view of electrode 12. FIG. 2B is a top view of electrode 12. FIG. 2C is a front view of electrode 12. FIG. 2D is a side view of electrode 12 and FIG. 2E is another side view showing the angle of electrode 12. FIG. 2E shows that the front surface of electrode 12 slants downward at an angle of 30 degrees. The front surface, however, does not come to a point at the bottom, but is slightly truncated forming a ridge 21. At the bottom, this ridge 21 is also angled as shown in the front view in FIG. 2C. This ridge 21 in the preferred embodiment is angled at 2 degrees. The ridge 21 gets larger as you move from the front of the device 10 back towards the batteries 11 and 15. Electrode 12 is the negative electrode.

FIGS. 3A, B, C, D, and E show electrode 14, the positive electrode. FIG. 3A is a perspective view of electrode 14. FIG. 3B is the top view of electrode 14. FIG. 3C is a front view of electrode 14. FIG. 3D is a side view of electrode 14. FIG. 3E shows the electrode from a side perspective view. This view shows some of the bottom of electrode 14. In FIG. 3A, one can see that the front of electrode 14 slants downward. Electrode 14 does not slant downward to a point just above the bottom of the electrode. Electrode 14 is also truncated. However the truncated portion also has a portion of the electrode 14 cut out from the bottom forming ridge 30. FIG. 3C, the front view of the electrode 14 shows the ridge 30 running from a point near the top of the electrode to a point on the other side of the electrode near the bottom. This ridge 30 in the preferred embodiment slants at approximately 13 degrees. FIG. 3E shows that the top portion of the electrode 14 is cut at an angle of approximately 30 degrees. In the preferred embodiment, this ridge is approximately 0.037 inches thick.

When the electrodes 12 and 14 are placed in the housing as shown in FIG. 1, the electrodes 12 and 14 overlap each other in the preferred embodiment by 0.029 inches. The electrodes 12 and 14 aligned such that when the needle is placed into collar 32 and into the device, the needle will make contact with both electrodes 12 and 14.

Figure 4B:
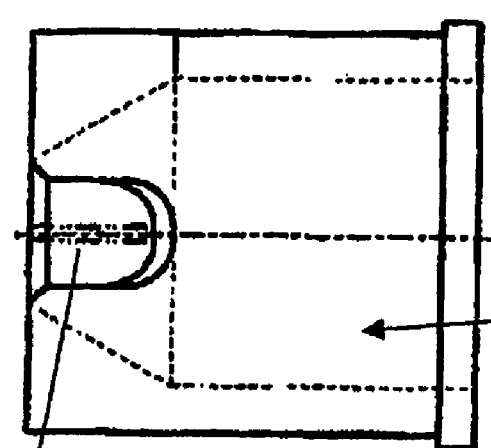
FIG. 4B is a side view of the collar of the invention.
Figure 4A:
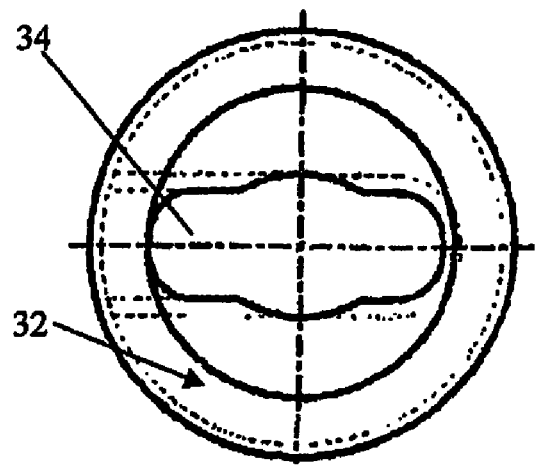
FIG. 4A is a top view of one of the collar of the invention.
Figure 4C:
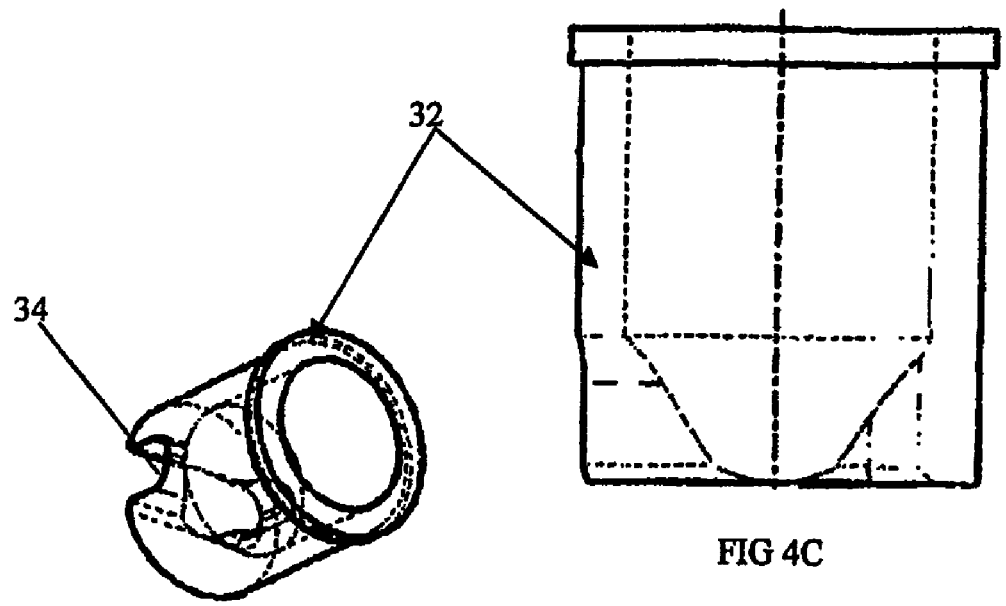
FIG. 4C is the opposite side view of the collar of the invention.
Figure 4D:
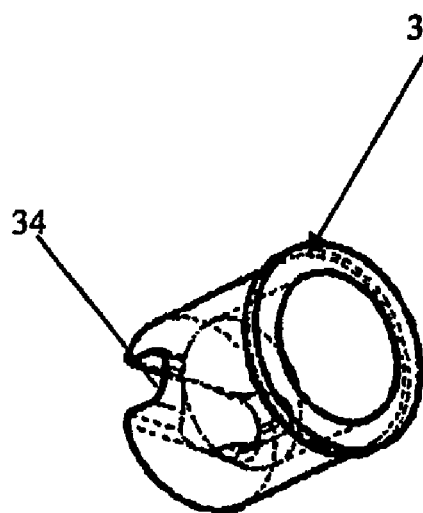

FIGS. 4A, B, C, and D shows the collar 32 of the invention. FIG. 4A shows the top view of the collar 32 of the invention. FIG. 4A shows that the collar 32 is basically cylindrical in shape with an opening 34 at the bottom. The opening 34 at the bottom is an ellipse with the sides slightly bowed out from a normal ellipse. FIG. 4B shows a side view of the collar 32 with the open area forming the center of the collar 32 in phantom. This shows that the collar 32 is cylindrical at the top; however, near the bottom, the collar 32 opening is conical. FIG. 4C is the opposite side of the collar 32, and it shows that the opening 34 at the bottom of the collar moves up the side of the collar on this side. The opening 34 forms a slight arch-type structure. FIG. 4D is a perspective view of the collar 32 that shows the cylindrical opening at the top and the arch-type opening at the one side, and also in phantom, shows the opening 34 at the bottom of the collar. The opening 34 at the bottom of the collar has been designed to accept any size of hypodermic known by the inventor and to place that hypodermic at the right point on the electrodes 12 and 14 so that the needle will be fully disintegrated.

Figure 5:
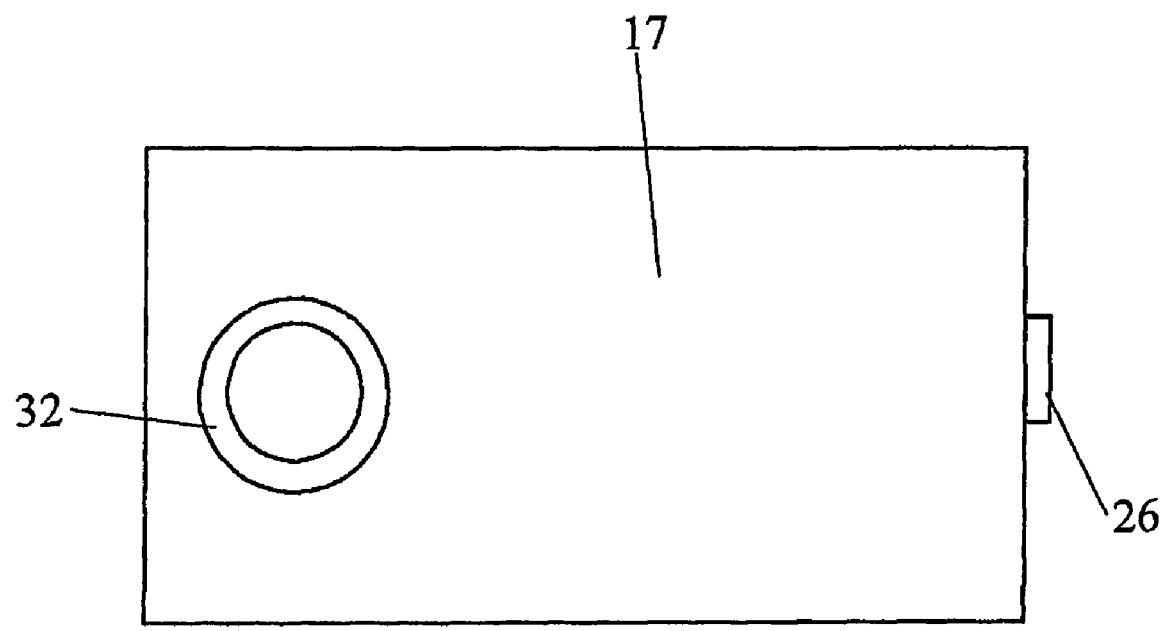
FIG. 5 is a top view of the invention with the top of the housing in place.

FIG. 5 is a top view of the invention. In FIG. 5 one can see the collar 32 which is where the needle end of the hypodermic needle is placed. The collar 32 is positioned on the housing 10 such that when the needle end of the hypodermic is placed in the collar 32 the needle will make contact with the electrodes 12 and 14 and be destroyed. FIG. 5 also show the jack 26 into which a 12 volt power supply such as a 12 volt wall transformer could be attached. The power supply hooked to the jack 26 could be used to power the electrodes 12 and 14 or the charge the batteries 11 and 15.

To use the invention, one places the needle end of a hypodermic needle in the collar 32 and slowly rocks the hypodermic in the collar 32. The hypodermic needle first makes contact with electrode 14, and then as it moves down, it makes contact with electrode 12. The electricity from the power supply 10 flows through electrode 12, up the hypodermic needle to electrode 14. The resistance of the hypodermic needle is very, very high. Thus, the electric flowing through the hypodermic needle quickly heats the hypodermic needle to a temperature where the needle disintegrates.

Changes and modifications in the specifically described embodiments can be carried out without departing from the scope of the invention which is intended to be limited only by the scope of the appending claims.

The invention claimed is:

1. Needle disabling device comprising:
   A. a housing, and,
   B. an opening in the housing that is of sufficient size that a hypodermic needle can fit through; and,
   C. a bottom electrode within the housing; and,
   D. a top electrode that has a ridge on its front edge and this ridge becomes the surface of the electrode that the needle when placed in the opening in the housing makes contact with the electrode, and said ridge encompass most of the whole front edge of the electrode and said ridge, surface slants toward the bottom electrode within the housing; and,
   E. said top and bottom electrodes are aligned such within the housing below the opening that when a needle is placed through the opening the electrodes make contact with the needle and said top electrode makes contact with the needle above a point at which the bottom electrode makes contact with the needle; and,
   F. a power supply connected to the electrodes such that when the needle is placed through the opening and makes contact with the top and bottom electrodes, the current from the power supply flows to one of the electrodes and then through the needle to the other electrode and said electrical energy is of sufficient power that when it flows through the needle, it causes the needle to disintegrate.

2. A needle disabling device as in claim 1 wherein:
   A. the top and bottom electrodes are stationary.

3. A needle disabling device as in claim 1 wherein:
   A. The power supply is a battery.

4. A needle disabling device as in claim 1 further comprising:
   A. a collar that fits within the opening and said collar has a elliptical aperture at its bottom such that when the needle is placed within the collar and rocked, the needle will pass through the elliptical aperture, and the needle will make contact wit the electrodes in such a way that the needle will be fully disintegrated when the power from the power supply is allowed to flow through the electrodes.

5. A needle disabling device as in claim 4 wherein:
   A. the elliptical aperture is designed such that many sizes of needles can be placed with the collar and the needle will pass through the elliptical aperture and the needle will make contact with the electrodes in such a way that the needle will be fully disintegrated when the power from the power supply is allowed to flow through the electrodes.

6. A needle disabling device as in claim 1 wherein:
   A. the power supply is fully contained within the housing.

7. A needle disabling device as in claim 6 wherein:
   A. the power supply can be recharged from a source outside the housing.

8. A needle disabling device as in claim 7 wherein:
   A. the power supply is rechargeable batteries.

9. A needle disabling device as in claim 1 wherein:
   A. the power supply is outside the housing.

10. A needle disabling device as in claim 9 further comprising:
    A. a second power supply is which is fully contained within the housing.

11. A needle disabling device as in claim 10 wherein:
    A. the second power supply can be recharged from a source outside the housing.

12. A needle disabling device as in claim 11 wherein:
    A. the second power supply is rechargeable batteries.

13. A needle disabling device comprising:
    A. a housing; and,
    B. a top electrode; and,
    C. a bottom electrode; and,
    D. an opening in the housing that is over the electrodes such that when a needle is placed through the opening, the metal end of the needle will make contact with both electrodes; and,
    E. a power supply attached to both electrodes and said power supply is of ample power that it will produce sufficient amount of energy to the electrodes so such that when a needle is placed in contact with both electrodes and completes the circuit, the needle will be disintegrated; and,
    F. a collar with a elliptical aperture in its bottom adapted to fit within the opening and said collar is adapted such that it will align many sizes of needles such that when the needle is placed within the collar and rocked, the needle will make contact with both electrodes in such a way that the needle will be fully disintegrated when the power from the power supply is allowed to flow through the electrodes.

14. A needle disabling device as in claim 13 wherein:
    A. the top and bottom electrodes are stationary.

15. A needle disabling device as in claim 13 wherein:
    A. said top electrode makes contact with the needle above a point at which the bottom electrode makes contact with the needle.

16. A needle disabling device as in claim 13 wherein:
    A. the power supply is fully contained within the housing.

17. A needle disabling device as in claim 16 wherein:
    A. the power supply can be recharged from a source outside the housing.

18. A needle disabling device as in claim 17 wherein:
    A. the power supply is rechargeable batteries.

19. A needle disabling device as in claim 13 wherein:
    A. the power supply is outside the housing.

20. A needle disabling device as in claim 19 further comprising:
    A. a second power supply is which is fully contained within the housing.

21. A needle disabling device as in claim 20 wherein:
    A. the second power supply can be recharged from a source outside the housing.

22. A needle disabling device as in claim 21 wherein:
    A. the second power supply is rechargeable batteries.

23. A needle disabling device as in claim 13 wherein:
    A. the power supply is a battery.

24. Needle disabling device comprising:
    A. a housing; and,
    B. an opening in the housing that is of sufficient size that a hypodermic needle can fit through; and, C. a bottom electrode shaped as a truncated triangular prism with its front surface slanting downward to the point of truncation forming a ridge and this ridge, as you move along its surface gets smaller and said electrode is within the housing; and, D. a top electrode within the housing; and, E. said top and bottom electrodes are aligned such within the housing below the opening that when a needle is placed through the opening and both electrodes make contact with the needle; and, F. a power supply connected to the electrodes such that when the needle is placed through the opening and makes contact with the top and bottom electrodes, the current from the power supply flows to one of the electrodes and then through the needle to the other electrode and said electrical energy is of sufficient power that when it flows through the needle, it causes the needle to disintegrate.

25. A needle disabling device as in claim 24 wherein:
A. the top and bottom electrodes are stationary.

26. A needle disabling device as in claim 24 wherein:
A. The power supply is a battery.

27. A needle disabling device as in claim 24 wherein:
A. the power supply is fully contained within the housing.

28. A needle disabling device as in claim 27 wherein:
A. the power supply can be recharged from a source outside the housing.

29. A needle disabling device as in claim 28 wherein:
A. the power supply is rechargeable batteries.

30. A needle disabling device as in claim 24 wherein:
A. the power supply is outside the housing.

31. A needle disabling device as in claim 30 further comprising:
A. a second power supply is which is fully contained within the housing.

32. A needle disabling device as in claim 31 wherein:
A. the second power supply can be recharged from a source outside the housing.

33. A needle disabling device as in claim 32 wherein:
A. the second power supply is rechargeable batteries.

34. A needle disabling device as in claim 24 further comprising:
A. a collar that fits within the opening and said collar has a elliptical aperture at its bottom such that when the needle is placed within the collar and rocked, the needle will pass through the elliptical aperture, and the needle will make contact with the electrodes in such a way that the needle will be fully disintegrated when the power from the power supply is allowed to flow through the electrodes.

35. A needle disabling device as in claim 34 wherein:
A the elliptical aperture is designed such that many sizes of needles can be placed with the collar and the needle will pass through the elliptical aperture and the needle will make contact with the electrodes in such a way that the needle will be fully disintegrated when the power from the power supply is allowed to flow through the electrodes.

36. A needle disabling device as in claim 24 wherein:
A. said top electrode makes contact with the needle above a point at which the bottom electrode makes contact with the needle.

37. Needle disabling device comprising:
A. a housing; and,
B. an opening in the housing that is of sufficient size that a hypodermic needle can fit through; and, C. A bottom electrode within the housing; and, D. a top electrode that is shaped like a truncated triangular prism and the electrodes surface slants downward to the point of truncation forming a ridge and this ridge becomes the surface of the electrode so that when the needle is placed in the opening in the housing and makes contact with both electrodes, the needle will make contact with the ridge of this electrode, and said ridge slants downward towards the bottom electrode and said top electrode is within the housing; and, E. said top and bottom electrodes are aligned such within the housing below the opening that when a needle is placed through the opening and both electrodes make contact with the needle; and, F. a power supply connected to the electrodes such that when the hypodermic needle is placed through the opening and makes contact with the top and bottom electrodes, the current from the power supply flows to one of the electrodes and then through the hypodermic needle to the other electrode and said electrical energy is of sufficient power that when it flows through the needle, it causes the needle to disintegrate.

38. A needle disabling device as in claim 37 wherein:
A. The power supply is a battery.

39. A needle disabling device as in claim 37 wherein:
A. the power supply is fully contained within the housing.

40. A needle disabling device as in claim 39 wherein:
A. the power supply can be recharged from a source outside the housing.

41. A needle disabling device as in claim 40 wherein:
A. the power supply is rechargeable batteries.

42. A needle disabling device as in claim 37 wherein:
A. the power supply is outside the housing.

43. A needle disabling device as in claim 42 further comprising:
A. a second power supply is which is fully contained within the housing.

44. A needle disabling device as in claim 43 wherein:
A. the second power supply can be recharged from a source outside the housing.

45. A needle disabling device as in claim 44 wherein:
A. the second power supply is rechargeable batteries.

46. A needle disabling device as in claim 37 further comprising:
A. a collar that fits within the opening and said collar has a elliptical aperture at its bottom such that when the needle is placed within the collar and rocked, the needle will pass through the elliptical aperture, and the needle will make contact with the electrodes in such a way that the needle will be fully disintegrated when the power from the power supply is allowed to flow through the electrodes.

47. A needle disabling device as in claim 46 wherein:
a the elliptical aperture is designed such that many sizes of needles can be placed with the collar and the needle will pass through the elliptical aperture and the needle will make contact with the electrodes in such a way that the needle will be fully disintegrated when the power from the power supply is allowed to flow through the electrodes.

48. A needle disabling device as in claim 37 wherein:
A. said top electrode makes contact with the needle above a point at which the bottom electrode makes contact with the needle.

* * * * *